US012150965B2

United States Patent
Chen et al.

(10) Patent No.: US 12,150,965 B2
(45) Date of Patent: Nov. 26, 2024

(54) **COMBINATION OF PROBIOTICS WITH *LACTICASEIBACILLUS PARACASEI* S38 AND *BACILLUS COAGULANS* BC198 AND APPLICATIONS THEREOF FOR IMPROVING BODY COMPOSITIONS**

(71) Applicant: Syngen Biotech Co., Ltd, Tainan (TW)

(72) Inventors: Wei-Jen Chen, Tainan (TW); Hui-Fang Chu, Tainan (TW); Yu-Lun Tsai, Kaohsiung (TW); Shiuan-Huei Wu, Taichung (TW); Chi-Fai Chau, Taichung (TW)

(73) Assignee: SYNGEN BIOTECH CO., LTD., Tainan (TW)

( * ) Notice: Subject to any disclaimer, the term of this patent is extended or adjusted under 35 U.S.C. 154(b) by 51 days.

(21) Appl. No.: 17/494,897

(22) Filed: Oct. 6, 2021

(65) Prior Publication Data

US 2023/0210919 A1    Jul. 6, 2023

(51) Int. Cl.
*A61K 35/742* (2015.01)
*A23L 33/135* (2016.01)
*A61K 35/744* (2015.01)

(52) U.S. Cl.
CPC .......... *A61K 35/742* (2013.01); *A23L 33/135* (2016.08); *A61K 35/744* (2013.01)

(58) Field of Classification Search
CPC .... A61K 35/742; A61K 35/744; A23L 33/135
See application file for complete search history.

(56) References Cited

FOREIGN PATENT DOCUMENTS

| CN | 110151796 A | * | 8/2019 | |
| WO | WO-2012142678 A1 | * | 10/2012 | ............. A23L 1/097 |

OTHER PUBLICATIONS

Mamoru Tanida et al, High-fat diet-induced obesity is attenuated by probiotic strain Lactobacillus paracasei ST11 (NCC2461) in rats, Obesity Research & Clinical Practice, vol. 2, Issue 3, 2008, pp. 159-169. (Year: 2008).*
Le Chatelier, E., Nielsen, T., Qin, J et al. Richness of human gut microbiome correlates with metabolic markers. Nature 500, 541-546 (2013). https://doi.org/10.1038/nature12506 (Year: 2013).*
Kim B, Kwon J, Kim M-S, Park H, Ji Y, Holzapfel W, et al. (2018) Protective effects of Bacillus probiotics against high-fat diet-induced metabolic disorders in mice. PLoS ONE 13(12): e0210120. https://doi.org/10.1371/journal.pone.0210120 (Year: 2018).*

(Continued)

*Primary Examiner* — Thomas J. Visone
(74) *Attorney, Agent, or Firm* — Muncy, Geissler, Olds & Lowe, P.C.

(57) ABSTRACT

A combination of probiotics for improving body compositions includes *Lacticaseibacillus paracasei* S38 and *Bacillus coagulans* BC198. The combination of probiotics can be a medicine composition, a nutrient supplement, healthy food or a combination thereof. The applications of the combination of probiotics include weight loss, reduction of fat, abatement of appetite, production of butyric acid within intestinal tracts and an increased count of *Akkermansia muciniphila* or Ruminococcaceae inside intestines.

3 Claims, 5 Drawing Sheets
(3 of 5 Drawing Sheet(s) Filed in Color)

Specification includes a Sequence Listing.

(56) References Cited

OTHER PUBLICATIONS

Cheng-En Hsieh et al (2020) Bacillus coagulans BC198 and Lactobacillus paracasei S38 in combination reduce body fat accumulation and modulate gut microbiota, CyTA—Journal of Food, 18:1, 764-775, DOI: 10. (Year: 2020).*

Chiou, W.-C. et al Synbiotic Intervention with an Adlay-Based Prebiotic and Probiotics Improved Diet-Induced Metabolic Disturbance in Mice by Modulation of the Gut Microbiota. Nutrients 2021, 13, 3161. (Year: 2021).*

Bengoa, A.A.; Dardis, C.; Garrote, G.L.; Abraham, A.G. Health-Promoting Properties of Lacticaseibacillus paracasei: A Focus on Kefir Isolates and Exopolysaccharide—Producing Strains. Foods 2021, 10, 2239. (Year: 2021).*

Aminlari et al., Probiotics Antimicro. Prot., 11:1163-1173 (2019) (Year: 2019).*

Urtasun et al., Nutrients, 12, 2504:1-19 (2020) (Year: 2020).*

* cited by examiner

COMBINATION OF PROBIOTICS WITH *LACTICASEIBACILLUS PARACASEI* S38 AND *BACILLUS COAGULANS* BC198 AND APPLICATIONS THEREOF FOR IMPROVING BODY COMPOSITIONS

The instant application contains a Sequence Listing which has been submitted electronically in the ASCII text file and is hereby incorporated by reference in its entirety. The ASCII text file is a sequence listing entitled "2021 Dec. 1-Seq-Listing" created on Dec. 1, 2021 and having a size of 2,831 bytes in compliance of 37 CFR 1.821.

BACKGROUND OF THE INVENTION

Field of the Invention

A combination of probiotics with *Lacticaseibacillus paracasei* S38 and *Bacillus coagulans* BC198 and applications thereof are disclosed in the present application. In the combination of probiotics, both *Lacticaseibacillus paracasei* S38 collected from feces in healthy youths' intestinal tracts and cultivated and *Bacillus coagulans* BC198 derived from green malts and cultivated prove effective in weight losses in a follow-up animal test and show an additive effect through administration of low-dosage S38 and BC198 for efficiencies of weight loss, reduction of adipose, generation of butyric acid at intestinal environment and counts of *Akkermansia muciniphila* and Ruminococcaceae within intestinal tracts. Furthermore, the combination of probiotics can be a medicine composition, a nutrient supplement, healthy food or a combination thereof.

Description of the Prior Art

As disclosed in a report issued by the World Health Organization in 2016, 39% and 13% adults in the whole world were classified as overweight and obese people, respectively. For countries in which the majority of global populations concentrate, people dying that are overweight or obese outnumbers people dying who are underweight.

In general, the options available to people for preventing or correcting obesity include surgery, drug therapy, dietary control, exercise and dietary supplements. As the option commonly accepted by people, probiotics in all dietary supplements are recognized as healthy food and popular with the general public.

However, not all of probiotics have an effect on weight loss. As disclosed in a literature published in 2016, *Lactobacillus kefiranofaciens* M1 promotes weight gains and lipogenesis (*Journal of functional foods*, 2016, 23:580-589). Furthermore, *Lacticaseibacillus casei* LcS ingested has no effect on changes in body weight or body fat (*Metabolism and Cardiovascular Diseases*, 2017, 27.10:910-918).

According to one concept commonly accepted by academia, obesity is the result of interactions between a human being and environment. It has been demonstrated by research that intestinal microbiota is a critical factor dominating an individual's obesity and featuring mechanisms such as changing calorie absorption, influencing lipid metabolism and changing appetite can be changed by diets. In addition, distinct bacteria perform their own functions. For example, *Akkermansia muciniphila* inhibits lipogenesis by correcting intestinal leakage and inflammation (*Frontiers in microbiology*, 2017, 8:1765), Ruminococcaceae abates appetite and corrects inflammation-induced obesity by secreting butyric acid, and Desulfovibrionaceae promotes lipogenesis through pro-inflammation.

Because intestinal bacteria are the critical factor to influence obesity, the measure for adjustment and control of the intestinal microbiota can be adopted for the effect of correcting obesity. Despite the general function of probiotics to change the intestinal microbiota, distinct probiotic strains make very different changes in the intestinal microbiota. Accordingly, the effects of a single bacterial strain on various properties such as intestinal microbiota, body weight and lipogenesis cannot be fully measured.

In virtue of fluctuant characteristics and functions between distinct bacterial strains, the effect of a single probiotic strain on weight loss should be verified through screening and demonstration.

Microbiota and/or body weight are probably regulated by distinct bacterial strains through dissimilar mechanisms. Furthermore, the functions of a plurality of bacterial strains cannot be derived from the functions of one single bacterial strain inside a composition because of possible interactions between probiotic strains. As disclosed in past research, there is no difference in the effect on correcting obesity between a combination of a plurality of bacterial strains and a single bacterial strain and the effect of a combination of a plurality of bacterial strains is worse than that of a single bacterial strain (*Obesity*, 2013, 21.12:2571-2578; *Nutrition, Metabolism and Cardiovascular Diseases*, 2017, 27.10:910-918). Accordingly, the effect of a combination of bacterial strains on anti-obesity should be demonstrated by practical tests.

The means to find a single bacterial strain or a combination of a plurality of bacterial strains to correct obesity and improve body compositions effectively is a critical issue settled in the present application.

SUMMARY OF THE INVENTION

A goal of the present invention is to provide *Lacticaseibacillus paracasei* S38 under the numbers of BCRC911007 and DSM33753 deposited with institutions for the effect of improving body compositions.

Another goal of the present invention is to provide *Bacillus coagulans* BC198 under the numbers of BCRC910916 and DSM33206 deposited with institutions for the effect of improving body compositions.

Another goal of the present invention is to provide a combination of probiotics which comprises *Lacticaseibacillus paracasei* S38 and *Bacillus coagulans* BC198 as mentioned previously for the effect of improving body compositions.

To this end, the combination of probiotics comprises viable probiotics; a formulation for the combination comprises a carrier agent, an excipient and a diluent; a formulation for the combination is selected from a group consisting of a solution, a suspension liquid, an emulsion, a powder, a pastille, a pill, a syrup, a troche, a tablet, a chewing gum, a thick juice and a capsule; the combination of probiotics is further manufactured as a liquid milk, a condense milk, a yogurt, a frozen yogurt, a lactobacillus fermented beverage, a milk powder, an ice cream, a cream, a cheese, a soybean milk, a fermented soybean milk, a vegetable juice, a fruit juice, a sports drink, a dessert, a jelly, a candy, a baby food, a healthy food, an animal food, a Chinese herbal medicine composition or a dietary supplement.

Another goal of the present invention is to provide a method for improving body compositions in a subject, comprising administering to the subject a combination of *Lacticaseibacillus paracasei* S38 and *Bacillus coagulans* BC198.

To this end, the applications of a combination of probiotics are effectuated through weight loss and reduction of body fat or visceral fat and prove effective in abatement of appetite, increase of butyric acid within intestinal tracts and proliferation of *Akkermansia muciniphila* or Ruminococcaceae. The applications for improving body compositions mean controlling weight gains and increased body fat or visceral fat after ingestions of high-fat diets. The dosage of *Lacticaseibacillus paracasei* S38 to be administrated ranges from $3.2 \times 10^9$ to $3.2 \times 10^{11}$ CFU (colony forming unit)/day; the dosage of *Bacillus coagulans* BC198 to be administrated ranges from $3.2 \times 10^9$ to $3.2 \times 10^{11}$ CFU (colony forming unit)/day.

In summary, *Lacticaseibacillus paracasei* S38 and *Bacillus coagulans* BC198, both of which are new bacterial strains selected herein, have the following advantages including inhibited lipogenesis in adipocytes, reduction of visceral fat, weight loss, decrease of body fat, abatement of appetite, increase of butyric acid within intestinal tracts and proliferation of *Akkermansia muciniphila* or Ruminococcaceae. Furthermore, good and unexpected synergistic effects are obtained after administration of both new bacterial strains, *Lacticaseibacillus paracasei* S38 and *Bacillus coagulans* BC198.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The techniques of present invention would be more understandable from the detailed description given herein below and the accompanying figures are provided for better illustration, and thus description and figures are not limitative for present invention, and wherein.

DETAILED DESCRIPTION OF THE INVENTION

Embodiment 1: Separation of the *Lacticaseibacillus paracasei* S38 (Hereinafter Referred to as S38) Strain Feces collected from intestinal tracts of young and healthy Taiwanese were placed into MRS broths in anaerobic environment for 24-hour cultivation at 37° C.; cultures in the broths were coated on an MRS agar plates in anaerobic environment for 3-day cultivation at 37° C. again; the single bacterial colony in agar culture medium was collected for further purification with which the bacilliform S38 strain with catalase negative was separated.

Embodiment 2: Bacteriologic Characteristics of the S38 Strain

Figure 1:
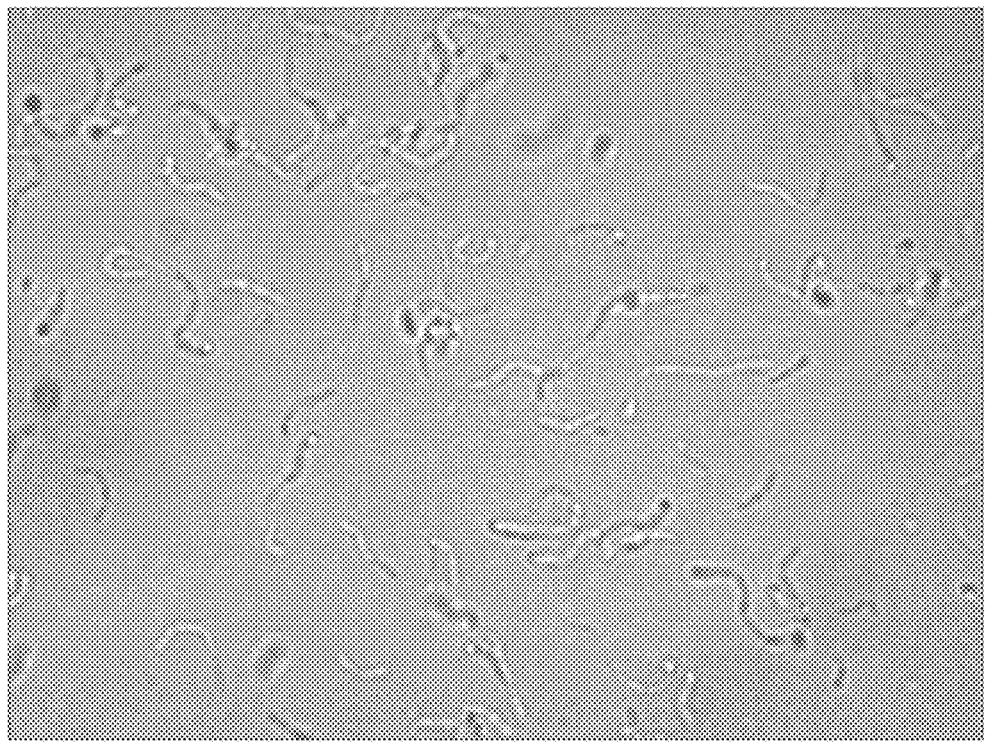
FIG. 1 illustrates the morphology of *Lacticaseibacillus paracasei* S38 microscopically.

Bacteriologic Characteristics of the S38 Strain are Shown as Follows:
Morphological Characteristics:
  Cell shape and Gram staining: Bacteria placed inside MRS broths in anaerobic environment for 24-hour cultivation at 37° C. displayed the curly feature of bacilli microscopically, as shown in FIG. 1.
  Activity: no
  Sporulation: no
  Gram staining: positive
Cultural Characteristics:
  Culture medium: MRS broth, pH=6.25
  Culture condition: anaerobic or aerobic environment at 37° C.
Physiological Characteristics:
  Catalase: negative
  Oxidase: negative Embodiment 3: Identification of the *Lacticaseibacillus paracasei* S38 Strain 16S rDNA sequencing analysis of the S38 strain: DNAs of the S38 strain were extracted for amplification of 16S rDNA (ribosomal DNA) gene segments; PCR (polymerase chain reaction) products derived were checked with agar gel electrophoresis for verification of the expected product size and sequencing as disclosed in SEQ ID NO: 1 (in the sequence table) for the 16S rDNA sequence of the S38 strain. The 16S rDNA sequence of the S38 strain was checked in the BLAST database of the National Center for Biotechnology Information (NCBI) and closest to the sequence of the *Lacticaseibacillus paracasei* strain HBUAS53050 according to the outcome of sequence alignment with the similarity of 99.89%.

Embodiment 4: Separation of the *Bacillus coagulans* BC198 (Hereinafter Referred to as BC198) Strain Green malts were added into sterile water that was ten times as heavy as green malts and smashed in a homogenizer for 10-minute gravity settling; supernatants were placed into MRS broths for 48-hour cultivation at 50° C. Next, cultures were coated on MRS agar plates in anaerobic environment for 3-day cultivation at 50° C.; the single bacterial colony on agar medium was collected and further purified for separation of the bacilliform BC198 strain with catalase positive.

Embodiment 5: Bacteriologic Characteristics of the BC198 Strain

Figure 2:
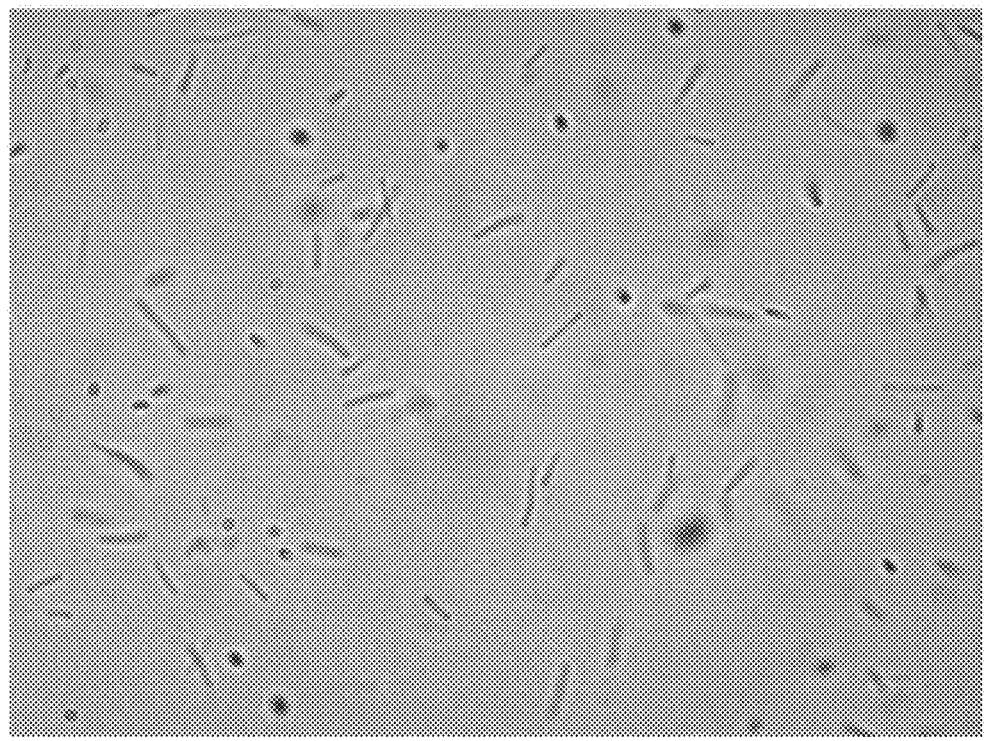
FIG. 2 illustrates the morphology of *Bacillus coagulans* BC198 microscopically.

Bacteriologic Characteristics of the BC198 Strain are Shown as Follows:
Morphological Characteristics:
  Cell shape and Gram staining: Bacteria placed on agar plates for 48-hour cultivation at 37° C. displayed morphology of bacilli microscopically and transformed to endospores partially, as shown in FIG. 2.
  Activity: yes Sporulation: yes
Gram staining: positive
Cultural Characteristics:
  Culture medium: MRS broth, pH=6.25
  Culture condition: anaerobic or aerobic environment at 45° C.
Physiological Characteristics:
  Catalase: positive Embodiment 6: Identification of the *Bacillus coagulans* BC198 Strain 16S rDNA sequencing analysis of the BC198 strain: DNAs of the BC198 strain were extracted for amplification of 16S rDNA gene segments; PCR products derived were checked with agar gel electrophoresis for verification of the expected product size and sequencing as disclosed in SEQ ID NO: 2 (in the sequence table) for the 16S rDNA sequence of the BC198 strain. The 16S rDNA sequence of the BC198 strain was checked in the BLAST database of the National Center for Biotechnology Information (NCBI) and closest to the sequence of *Bacillus coagulans* strain 4086 according to the outcome of sequence alignment with the similarity of 100.00%.

Embodiment 7: Effect of Administration of Both S38 and BC198 on Inhibiting Lipogenesis at 3T3-L1 Cells 7.1 Preparation of Fermentation Broth Samples The S38 strain and two other *L. paracasei* strains from the Bioresource Collection and Research Center (BCRC at Hsinchu, Taiwan) were cultivated in MRS broths at 37° C. for 24 hours separately. The BC198 strain and three *B. coagulans* strains commercially available and separated from dried funguses were cultivated in MRS broths at 45° C. for 24 hours separately. After cultivation, culture medium was centrifuged (10,000 RCF; 10 minutes) and supernatants collected as fermentation broth samples were placed in water baths at 70° C. for 30 minutes. The fermentation broth samples were inoculated in MRS broths for 4-day cultivation at 37° C. after which no sign of growth, i.e., no viable bacteria, was observed.

7.2 Design of a Cell Experiment

Mice's preadipocytes, i.e., 3T3-L1 cell lines (BCRC 60159), purchased from BCRC were cultivated in basal medium (DMEM with 10% fetal calf serums) at conditions of 37° C. and 5% $CO_2$.

3T3-L1 cells were implanted in 60 mm Petri dishes ($3 \times 10^5$ cells/dish). With cultivation completed in 70-80% of a Petri dish, adipocyte differentiation reagents (0.5 mM methylisobutylxanthine+1 μM dexamethasone+10 μg/mL insulin) were dispensed in basal medium for 48-hour induced differentiation after which old culture medium was removed and replaced by general culture medium including 10 μg/mL insulin and 1% (v/v) samples. After 48-hour cultivation, the culture medium was removed again and replace by basal medium with 1% (v/v) samples for 48-hour cultivation. In the control group, no sample was added into medium.

For oil red staining conducted on 3T3-L1 cells, the content of lipids was quantified with reference to the spectrophotometer. Furthermore, for oil red staining conducted on 3T3-L1 cells which had been differentiated to adipocytes with reference to the method of Kraus et al. (Adipocyte, 2016, 5.4:351-358), the content of lipids was further quantified by the spectrophotometer. For that matter, the content of lipids for the control group was specified as 100%.

As mentioned previously, two independent tests were conducted from step 1 to step 3.

7.3 Statistical Method

Two quantitative test results for the content of lipids are denoted by "mean±variance". All fermentation broth samples for different groups are compared with the control group by the Student's t-test. $p<0.05$ (*) is taken as significant discrepancy.

7.4 Inhibition of Lipogenesis

Figure 3:
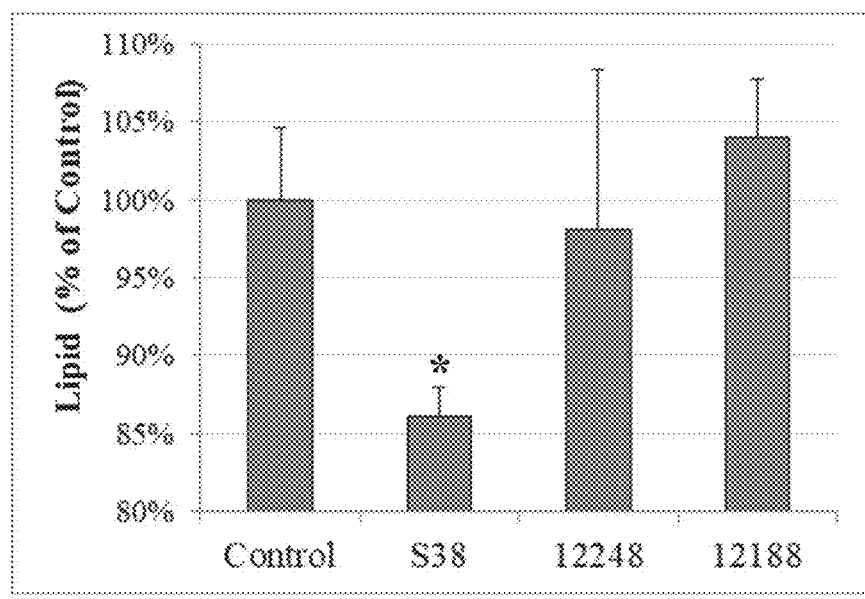
FIG. 3 illustrates a comparative result for inhibition of lipogenesis in adipocytes by *Lacticaseibacillus paracasei* S38.

As shown in FIG. 3, lipogenesis of adipocytes is inhibited by the S38 strain only among three *L. paracasei* strains and the statistical discrepancy is observed.

Figure 4:
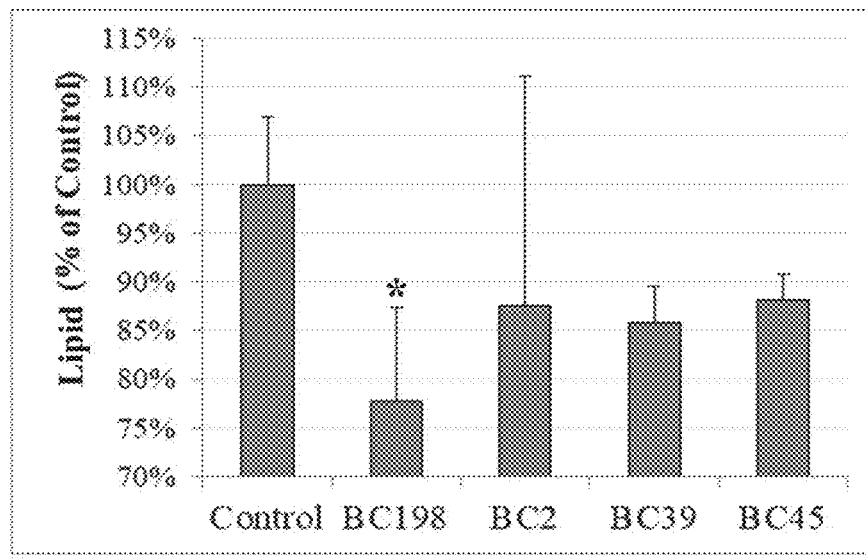
FIG. 4 illustrates a comparative result for inhibition of lipogenesis in adipocytes by *Bacillus coagulans* BC198.

As shown in FIG. 4, lipogenesis of adipocytes is inhibited by each of four *B. coagulans* strains but the statistical significance is observed in BC198 only which displays a good effect almost twice stronger than other *B. coagulans* strains.

Embodiment 8: Effect on Correcting Obesity Through Administration of Both S38 and BC198

8.1 Animal Experiment Method

The experimental model was based on probiotics and high-fat diets, both of which were used in inducting the animal model of obesity. The eight-week male Sprague-Dawley rats bred in an environment with ambient temperature of 22±2° C. and the dark-light cycle every 12 hours were free to eat food. Rats of the 5 NC group were continuously provided with normal diets which contained 5% (w/w) fat (3.4 kcal/g) during the experiment; rats of the HF group were provided with high-fat diets which contained 22.5% (w/w) fat (4.3 kcal/g). The ingredients of diets fed to rats of NC and HF groups are shown in Tables 1A and 1B.

TABLE 1A

| Composition of experimental diets (g/100 g) | | |
|---|---|---|
| Ingredient | Group | |
| (g/100 g) | NC | HF |
| Chow[1] | 100.0 | 54.0 |
| Soybean oil | | 4.8 |
| Condensed milk[2] | | 28.5 |
| Lard | | 12.7 |

[1]Chow (PMI Nutrition International, St Louis, MO, USA) contained crude protein (23.9 g/100 g), crude lipid (5.0 g/100 g), and carbohydrate (48.7 g/100 g)
[2]Condensed milk contained crude protein (7.3 g/100 g), crude lipid (8.2 g/ 100 g), and carbohydrate (54.5 g/100 g).

TABLE 1B

| Composition of experimental diets (%) | | |
|---|---|---|
| Ingredient | Group | |
| (%) | NC | HF |
| Carbohydrate (%) | 48.7 | 41.7 |
| Fat (%) | 5.0 | 22.5 |
| Protein (%) | 23.9 | 15.0 |
| Enengy[1] (kcal/g) | 3.4 | 4.3 |

[1]Energy (kcal/g) ± (carbohydrate % × 4 + fat % × 9 + protein % × 4)/100

The experimental groups were denoted as S38-L, S38-H, BC198-L, BC198-H and S38+BC198: rats of S38-L and S38-H were fed with S38 $5 \times 10^7$ and $5 \times 10^9$ CFU (colony forming unit/day through tube feeding, respectively; rats of BC198-L and BC198-H were fed with BC198 $5\times10^7$ and $5\times10^9$ CFU/day through tube feeding, respectively; rats of S38+BC198 were fed with BC198 $5\times10^7$ as well as S38 $5\times10^7$ or $1\times10^8$ CFU/day totally through tube feeding.

During the 12-week animal experiment, the dietary intakes of rats were measured and recorded every day and a rat's precise weight was checked once daily before eating. Each rat's fecal samples were collected and stored at temperature of $-20°$ C. in the last three days of the animal experiment for follow-up microbiome analysis.

8.2 Experimental Indicator

1. Body weight: a rat's weight was checked every day; weight gain $(g)$=final weight$(g)$-initial weight$(g)$ 2. Total calorie intake: dietary intake/day×food's calories
3. Weight of visceral fat: Perirenal fat, mesentery fat and epididymal fat collected after the experiment were weighed (Chu et al., Agricultural and Food Chemistry, 2014, 62:192-197). The weight of total visceral fat is defined as the sum of weights of perirenal fat, mesentery fat and epididymal fat; the percentage of the weight of total visceral fat accounting for the body weight is calculated by the following formula:

Percentage of total visceral fat(%)=(Weight of total visceral fat/final weight)×100%

4. Liver lipids: The content of liver total lipids extracted through n-hexane and methanol (ratio=2:1,v/v) as extracting solvents was quantified (Folch et al., (1957), *Journal of Biological Chemistry*, 1957, 226:497-509).
5. Fecal short-chain fatty acids (fecal SCFAs): Fecal SCFAs were checked by a gas chromatograph with which the contents of acetic acid, propanoic acid and butyric acid in samples were analyzed (Kao et al., (2018), *Molecules*, 2018, 23:1-9) based on following conditions:

Tubular column: Agilent J and W HP-INNO Wax GC Column (30 m; 0.25 mm; 0.25 μm)

Mobile phase: helium
Flow rate: 7 mL/min
Injected sample volume: 1 μL
Program design: initial temperature of 80° C. (1 minute)→140° C. (1 minute)→220° C. (2 minutes)
Injector temperature: 140° C.
Sensor temperature: 250° C.

8.3 Statistical Method

Experimental results are denoted by "mean±standard deviation (SD)". With SPSS taken as the package software for statistic analysis, data is checked by one-way ANOVA and the differences in samples between groups are checked by Duncan's multiple range test. The p-value<0.05 means significant discrepancy marked with a, b or c, as shown in the following tables.

8.4 Effects on Reducing Body Weight and Abating Appetite Through Administration of Both S38 and BC198

As shown in Table 2, administration of both S38 and BC198 contributes to inhibiting a weight gain. Despite the effect of S38 (BC198) on inhibition of a weight gain susceptible to high-fat diets and significantly reduced by high-dosage S38 (BC198), there is no statistical discrepancy observed in rats of a single group, which were fed with S38 (BC198) only. Furthermore, despite the dosage ($1\times10^8$) of both BC198 and S38 administrated to rats much less than the dosage ($5\times10^9$) of a single strain administrated, the fact that the effect of both BC198 and S38 administrated together on inhibition of a weight gain is significantly better than that of a single strain administrated suggests synergy existing between BC198 and S38.

TABLE 2

Body weights among different groups

| Group | Initial weight (g) | Final weight (g) | Weight gain (g) |
|---|---|---|---|
| NC | 373.1 ± 18.7a | 563.9 ± 13.1c | 190.8 ± 12.5c |
| HF | 377.7 ± 10.1a | 664.1 ± 47.9a | 286.5 ± 41.3a |
| BC198-L | 394.2 ± 20.7a | 673.6 ± 23.4a | 279.4 ± 24.0a |
| BC198-H | 374.6 ± 17.1a | 638.2 ± 35.4ab | 263.6 ± 39.7ab |
| S38-L | 393.0 ± 26.6a | 655.2 ± 39.8a | 262.2 ± 15.9ab |
| S38-H | 383.7 ± 14.0a | 629.6 ± 74.9ab | 245.9 ± 61.8ab |
| BC198 + S38 | 373.8 ± 15.7a | 591.8 ± 68.8bc | 217.9 ± 56.2bc |

It can be seen from Table 3 that administration of both S38 and BC198 is conductive to abating appetite. From data of caloric intakes in all groups, BC198 works against abatement of appetite but S38 appears to have the effect on abatement of appetite slightly. Moreover, it is surprisingly found that the dosage ($1\times10^8$) of both BC198 and S38 administrated to rats is much less than the high dosage ($5\times10^9$) of a single strain administrated and significantly credited with abatement of appetite. Thus, the good effect on abatement of appetite may be attributed to synergy between BC198 and S38, both of which were based on a low-dosage combination for administration.

TABLE 3

Total calorie intakes among different groups

| Group | Total caloric intakes (kcal) |
|---|---|
| NC | 7123 ± 174c |
| HF | 8760 ± 920ab |
| BC198-L | 9532 ± 760a |
| BC198-H | 8752 ± 829ab |
| S38-L | 8573 ± 655b |
| S38-H | 8313 ± 1024b |
| BC198 + S38 | 8018 ± 468b |

8.5 Effect on Inhibiting Lipogenesis Through Administration of Both S38 and BC198

As shown in Table 4, administration of both S38 and BC198 contributes to inhibiting the total visceral fat. Despite the effect of S38 (BC198) on inhibition of visceral fat accumulation susceptible to high-fat diets and significantly reduced by high-dosage S38 (BC198), there is no statistical discrepancy observed in rats of a single group, which were fed with S38 (BC198) only. It is surprisingly found that total visceral fat accumulation is significantly inhibited by administration of both BC198 and S38 which is better than administration of BC198 or S38 only.

The weights of perirenal fat, mesenteric fat and epididymal fat in different viscera are summarized in Table 4. Despite no significant difference in affecting or inhibiting fat accumulation between BC198 and S38 and high-dosage BC198 or S38 conductive to inhibition of fat accumulation in general, it is surprisingly found that the effect of administration of both BC198 and S38 on inhibition of fat accumulation is significantly better than that of administration of BC198 or S38 only.

TABLE 4

Relative size of visceral fat pads among different groups

| Group | Total visceral fat (g/100 g BW) | Perirenal fat (g/100 g BW) | Mesenteric fat (g/100 g BW) | Epididymal fat (g/100 g BW) |
|---|---|---|---|---|
| NC | 5.51 ± 0.87c | 2.30 ± 0.15c | 1.48 ± 0.39c | 1.73 ± 0.35c |
| HF | 11.26 ± 1.30a | 5.00 ± 0.76a | 2.86 ± 0.61ab | 3.40 ± 0.40a |
| BC198-L | 10.85 ± 2.02a | 4.69 ± 0.96a | 2.98 ± 0.72a | 3.17 ± 0.49a |
| BC198-H | 10.37 ± 0.94a | 4.61 ± 0.44a | 2.85 ± 0.30ab | 2.91 ± 0.58ab |
| S38-L | 10.32 ± 0.88a | 4.57 ± 0.71a | 2.82 ± 0.15ab | 2.93 ± 0.34ab |
| S38-H | 9.56 ± 1.09a | 4.37 ± 0.64a | 2.69 ± 0.29ab | 2.50 ± 0.36b |
| BC198 + S38 | 7.90 ± 1.90b | 3.15 ± 0.71b | 2.27 ± 0.54b | 2.48 ± 0.68b |

As shown in weights of liver total lipids in Table 5, liver lipid accumulation attributed to high-fat diets is inhibited by BC198 or S38, each of which is conductive to inhibiting more liver lipid accumulation by a high dosage, but statistical discrepancy is observed in S38-H. It is surprisingly found that liver lipid accumulation is significantly inhibited by administration of both BC198 and S38, which is better than administration of BC198 or S38 only.

TABLE 5

Liver total lipids among different groups

| Group | Liver total lipids(mg/g) |
|---|---|
| NC | 157.78 ± 8.62d |
| HF | 289.00 ± 60.47a |
| BC198-L | 269.38 ± 27.26ab |
| BC198-H | 250.70 ± 24.21ab |
| S38-L | 259.83 ± 35.04ab |
| S38-H | 233.11 ± 8.82b |
| BC198 + S38 | 195.72 ± 22.01c |

The positive synergy is credited with administration of both BC198 and S38. It can seen from analyses of visceral fats and liver lipids that BC198 or S38 contributes to inhibiting lipogenesis. However, it is surprisingly found that the dosage ($1\times10^8$ CFU/day) of administration of both BC198 and S38 is much less than the dosage ($5\times10^9$ CFU/day) of administration of BC198 or S38 only but significantly credited with inhibition of fat accumulation in contrast to administration of BC198 or S38 only. Thus, unexpected synergy is observed in administration of both BC198 and S38 and a combination of low-dosage BC198 and S38 performs better than anticipated.

8.6 Effect of Administration of Both BC198 and S38 on Generation of Short-Chain Fatty Acids As shown in Table 6, BC198 or S38 promotes generation of acetic acid, inhibits generation of propanoic acid and has no significant effect on generation of butyric acid. Administration of both BC198 and S38 as compound strains contributes generation of acetic acid but has no effect on generation of propanoic acid. It is surprisingly found that administration of both BC198 and S38 significantly promotes generation of butyric acid. That is, an unexpected effect is created from compound strains which induce generation of plenty of butyric acid based on low-dosage administration.

TABLE 6

Fecal SCFAs among different groups

| Group | Acetic acid µmol/g | Propanoic acid (µmol/g) | Butyric acid (µmol/g) |
|---|---|---|---|
| NC | 174 ± 40b | 73.0 ± 36.7a | 25.7 ± 15.7c |
| HF | 129 ± 55b | 50.0 ± 22.1ab | 50.2 ± 20.6b |
| BC198-L | 175 ± 35b | 31.2 ± 12.6b | 44.0 ± 5.3bc |
| BC198-H | 174 ± 24b | 34.3 ± 14.9b | 45.8 ± 8.2b |
| S38-L | 258 ± 44a | 46.5 ± 18.3ab | 50.3 ± 17.7b |
| S38-H | 288 ± 45a | 48.5 ± 15.1ab | 43.8 ± 21.9bc |
| BC198 + S38 | 252 ± 64a | 68.5 ± 16.1a | 100.2 ± 5.8a |

It has been known that a mechanism for obesity treatment related to butyric acid works as explained below: (1) secretions of PYY and GLP-1 to abate appetite; (2) moderation of intestinal leakage and inflammation to inhibit lipogenesis attributed to high-fat diets; (3) secretion of mucus from intestinal mucosae for increased abundance of *Akkermansia muciniphila* living on mucus and inhibition of lipogenesis. The test data for butyric acid which proves effective in inhibiting obesity approximately matches the outcomes of administration of both BC198 and S38 better than administration of BC198 or S38 only for body weight, percentage of fat and content of lipid.

Embodiment 9: Effect of Administration of Both BC198 and S38 on Changes of Intestinal Microbiota 9.1 Test Group:

In the animal test data of moderation of weight gains and inhibition of lipogenesis, single strain administration only in high dosage achieve good effects. Thus BC198 or S38 single strain with high dosage used in followed experiment. Accordingly, feces collected from six rats in each group for NC, HF, BC198-H, S38-H and BC198+S38 was analyzed in order to check the effects of single as well as compound probiotics on the whole intestinal microbiota and a species closely related to obesity and intentionally realize any interaction between compound strains.

9.2 Method for Analysis of Microbiota

Figure 5:
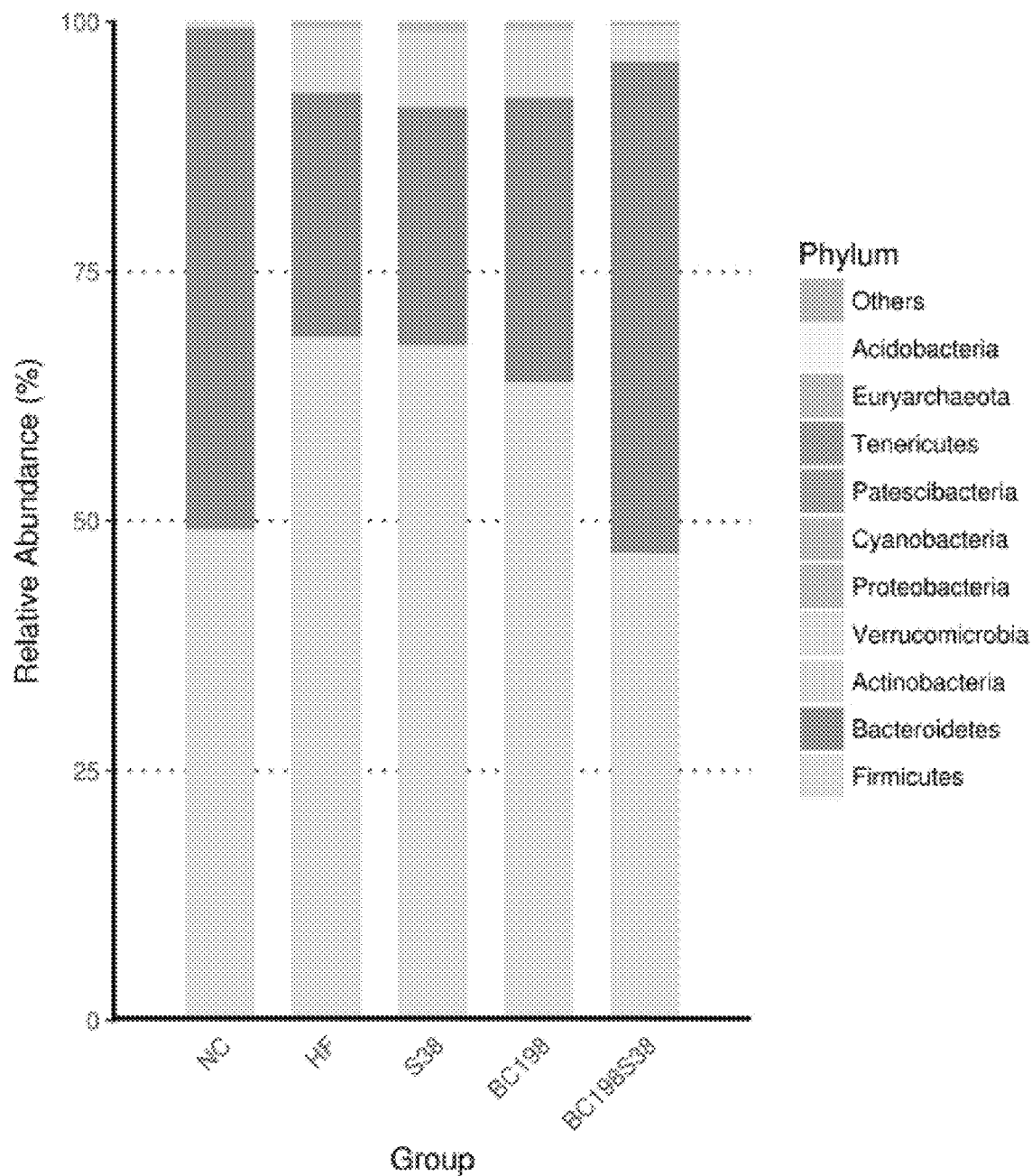
FIG. 5 is a histogram for relative abundances of species in the phylum level.

Biotools Co., Ltd. was commissioned to analyze the intestinal microbiota. With a bacterium' 16S rDNA genes taken as the target of sequencing in general, the research for microbes accompanied with the next-generation sequencing technology is used to identify all bacterial species in a biological sample. There are ten conserved regions and nine hypervariable regions in a bacterium' 16S rDNA gene sequence. For different bacterial species, there is no significant difference in the sequence for conserved regions with which a genetic relationship between biological species can be checked. For different bacterial genus and species, the sequence for hypervariable regions are diversified and used to check any difference between species. Based on the two mentioned characteristics, the sequencing strategy for a bacterium's DNAs extracted from feces relies on the polymerase chain reaction (PCR) to amplify conserved regions of the rDNA gene; the amplified segment covers partial hypervariable regions as the basis of identifying and analyzing a bacterial species after next-generation sequencing (NGS). The procedure for a sample sequencing is shown as follows:

Preparation of samples→extraction and purification of DNAs→PCR amplification→purification of products→creation of sample data sequencing for deriving raw tags→sequence assembly→clean tags after filtration→effective tags for follow-up analyses after removals of chimeras→OTUs (Operational Taxonomic Units) clustering (by sequence similarity, e.g., more than 97%) and species taxonomy analyses based on effective tags 9.2 Effect on the Intestinal Microbiota in the "Phylum" Level The top-ten species with relative abundances in the phylum level taxonomically were selected from test groups for development of a histogram for relative abundances of species in the phylum level from which species of test groups with high relative abundances in the phylum level and ratios thereof are checked directly and "other" means the total percentage of relative abundances for other species except those top-ten species in the phylum level. In the histogram for relative abundances of species in the phylum level in FIG. 5, intestinal bacteria of NC rats without the obesity symptom are taken as the normal microbiota. High-fat diets foster Firmicutes but restrain Bacteroidetes in the HF group. Either S38-H or BC198-H does not trigger proliferation of Firmicutes as well as Bacteroidetes significantly. Surprisingly, administration of both BC198 and S38 almost recovers the normal microbiota of Firmicutes and Bacteroidetes. Moreover, that fact that proliferation of Verrucomicrobia is facilitated by administration of both BC198 and S38 rather than BC198-H or S38-H suggests unexpected synergy due to administration of both BC198 and S38.

Figure 6:
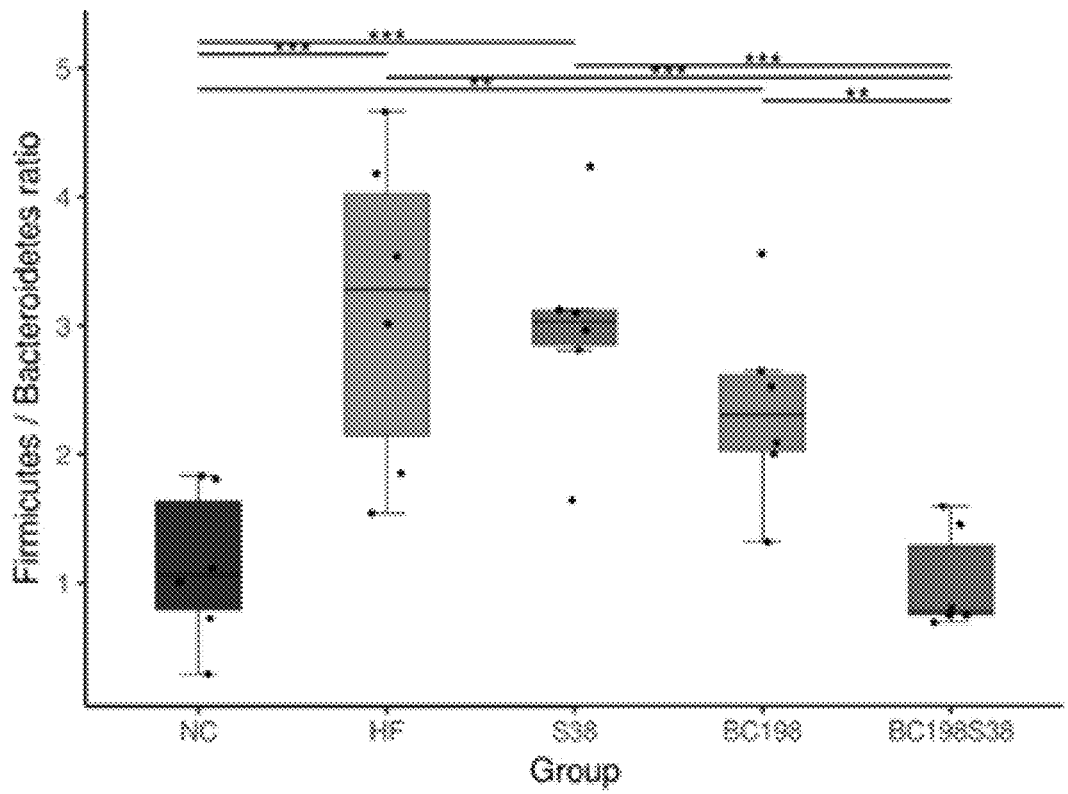
FIG. 6 illustrates the Firmicutes/Bacteroidetes ratio.

The Firmicutes/Bacteroidetes ratio (F/B ratio) is one factor to assess risks of a specific disease in researches of microbes recently. As disclosed in literatures, there is a correlation between a relatively higher F/B ratio and obesity. In general, the box plot, which denotes F/B ratios of all samples in test groups under different conditions, is a tool to explore meanings of a F/B ratio in research or disease diagnosis wherein a p-value is decided by the Kruskal-Wallis test (: p-value<0.01 between two groups; *: p-value<0.001 between two groups), as shown in FIG. 6. For that matter, the increased F/B ratio of the HF group is attributed to supply of high-fat diets but not affected by S38-H or BC198-H. It is surprisingly found that a F/B ratio decreases significantly and approximates the F/B ratio of the NC group with the normal microbiota due to administration of both BC198 and S38. Moreover, this finding suggests imbalance in the microbiota attributed to high-fat diets is corrected by administration of both BC198 and S38 for existence of unexpected synergy.

9.3 Principal Component Analysis (PCA)

Figure 7:
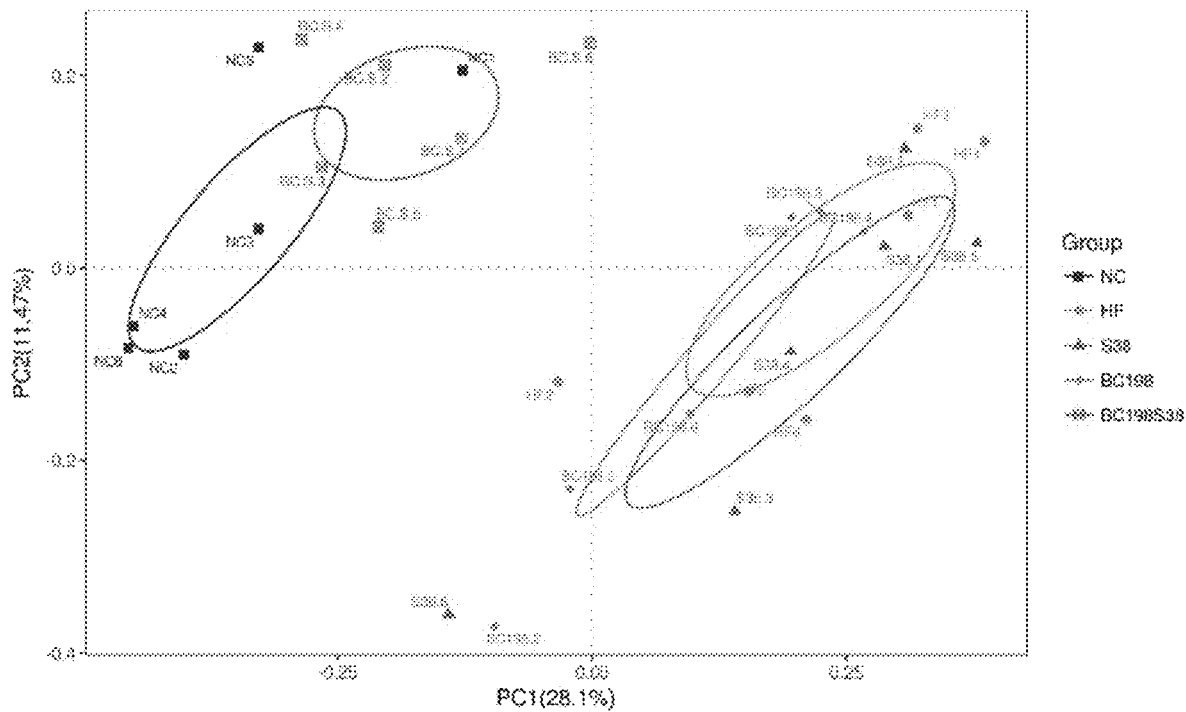
FIG. 7 illustrates the Principal Component Analysis (PCA) of bacterial colonies.

PCA, which relies on variance decomposition for dimensionality reduction on multidimensional data and keeps contribution of two variances in a dataset maximized simultaneously, is known for its method to find the principal components and structure from data effectively. Capitalizing on PCA, a researcher will find a coordinates axis which best reflects differences between samples such that differences in multidimensional data are displayed on two-dimensional coordinates through the linear combination and differences between individuals or groups are detected. The more similar compositions of sample colonies grow, the closer the distance between two sample colonies in a PCA plot approaches. In a PCA plot, the x-coordinate, the y-coordinate and the percentage denote the first principal component, the second principal component and the contribution rate of a principal component to a sample difference, respectively. The sample mean of each test group is marked as the center of a normalized confidence ellipse. In a PCA plot, each point denotes one sample and samples in an identical test group are labeled with the same color. As shown in FIG. 7, the distribution of different bacteria colonies is clearly decided through PCA for assessing any improvement of microbiota by samples. It can be seen from FIG. 7 that the microbiota distribution of the HF group significantly different from that of the NC group suggests the imbalanced intestinal microbiota of the HF group. The microbiota distribution of BC198-H (S38-H) is slightly changed but still next to the microbiota distribution of the HF group. However, different from the microbiota distribution of the HF group significantly, the microbiota distribution of the BC198+S38 group next to that of the NC group very much suggests unexpected synergy after administration of both BC198 and S38 that corrects imbalance of the intestinal microbiota attributed to high-fat diets.

9.4 Effect on the Intestinal Microbiota in "Family", "Genus" and "Species" Levels Microbiota plays a role to regulate and control a mechanism such as body weight and lipid metabolism. Accordingly, administration of both BC198 and S38 proves effective in correcting obesity by changing the abundance of a specific microbe probably. To further delve any change of the intestinal microbiota, the applicant referred to annotation information and abundance information of species for family and genus levels of all test groups taxonomically and selected top-35 species with individual abundances in family and genus levels. With the mean abundance of all samples taken as the abundance of a single group, a heatmap is drawn through clustering for the species level such that those species in samples with higher or lower abundances are discovered. As shown in outcomes in FIG. 8, the x-coordinate, the y-coordinate and the left-hand side as well as the top denote test groups, annotation information of species and the clustering tree of species, respectively. It can be seen from the heatmap for the clustering tree of species in the family level or the genus level taxonomically that the relative abundances of microbiota in HF, BC198-H and S38-H groups are similar to one another (a cluster on the x-coordinate) and the relative abundances of microbiota in NC and BC198+S38 groups are similar to each other (another cluster on the x-coordinate). In 35 OTUs in family and genus levels, abundances of partial OTUs are slightly changed by BC198-H or S38-H. However, it is surprisingly found that abnormal microbiota attributed to high-fat diets is significantly changed by administration of both BC198 and S38 and next to that of the NC group. Thus, this finding suggests imbalance of intestinal bacteria attributed to high-fat diets is corrected by administration of both BC198 and S38 for existence of unexpected synergy.

Some proven facts in the genus level are shown as follows. A positive correlation exists between Coriobacteriaceae and increased cholesterol (lipid molecules) absorption in obese people. Desulfovibrionaceae in the intestinal microbiota of obese people triggers intestinal inflammation responses and subsequently gives rise to metabolic dysfunction. A correlation exists between the increased abundance of Peptostreptococcaceae and high-calorie diets. The abundance of Coriobacteriaceae, Desulfovibrionaceae or Peptostreptococcaceae, each of which aggravates obesity, is alleviated by either BC198-H or S38-H for inhibition of lipogenesis and further restrained by administration of both BC198 and S38 with the dosage as little as 1/50 of BC198 or S38 only.

In addition, the abundance of Burkholderiaceae, which is accumulated in stromal vascular fractions of adipose tissues in overweight or obese people, is directly proportional to the body mass index. A positive correlation exists between Erysipelotrichaceae in the fecal microbiota of a creature ingesting high-fat diets and an obesity phenotype. Interestingly, the abundance of either Burkholderiaceae or Erysipelotrichaceae is slightly enhanced by BC198-H or S38-H but surprisingly alleviated by administration of both BC198 and S38 for correction of obesity.

The fact that a negative correlation exists between Ruminococcaceae with lots of crucial butyrate-producing bacteria and non-alcoholic fatty liver diseases or intestinal leaking suggests a positive effect of Ruminococcaceae on correction of obesity. It is surprisingly found that Ruminococcaceae is alleviated by BC198-H or S38-H but the abundance of Ruminococcaceae is enhanced by administration of both BC198 and S38. Thus, obesity can be corrected by increased Ruminococcaceae through administration of both BC198 and S38.

In the genus level, the positive correlation between Romboutsia and lipid synthesis in a liver is demonstrated. The abundance of Romboutsia is alleviated by BC198-H or S38-H and further inhibited by administration of both BC198 and S38, which proves effect in restraining lipogenesis in a liver.

For Akkermansiaceae of Verrucomicrobia, *Akkermansia muciniphila* is the only species living in rats. Accordingly, Akkermansiaceae in the heatmap is regarded as *Akkermansia muciniphila*. It has been demonstrated that lipogenesis is substantially inhibited by *Akkermansia muciniphila*, for example, Amuc_1100, a protein produced by *Akkermansia muciniphila*, is competent in inhibiting lipogenesis independently (Nature Medicine, 2017, 23.1:107-113). Interestingly, the abundance of *Akkermansia muciniphila* unaffected by BC198-H or S38-H but exponentially enhanced by administration of both BC198 and S38 suggests that unexpected synergy is facilitated by administration of both BC198 and S38 as one principal mechanism to inhibit obesity effectively.

The increased abundance of *Akkermansia muciniphila*, which produces propanoic acid and promotes proliferation of butyrate-producing bacteria, accords with the fact of more propanoic acid and butyric acid in feces of rats in the BC198+S38 group. The only carbon source available to *Akkermansia muciniphila* is mucin secreted from the mucous layer. For that matter, more mucin is secreted at the existence of butyric acid and provided to *Akkermansia muciniphila* for growth. Thus, another mechanism related to administration of both BC198 and S38 for effective inhibition of obesity is to increase the abundance of butyrate-producing bacteria, for example, Ruminococcaceae, and the output of butyric acid.

As previously mentioned for test results of the intestinal microbiota, imbalance of some microbiota such as Coriobacteriaceae and Desulfovibrionaceae induced by high-fat diets will be corrected by BC198-H and S38-H. However, despite synergy under administration of both BC198 and S38, unexpected changes in the microbiota work against the process of correcting the microbiota to normal status in which specific bacteria beneficial to fat losses such as *Akkermansia muciniphila* and Ruminococcaceae proliferate.

Figure 8:
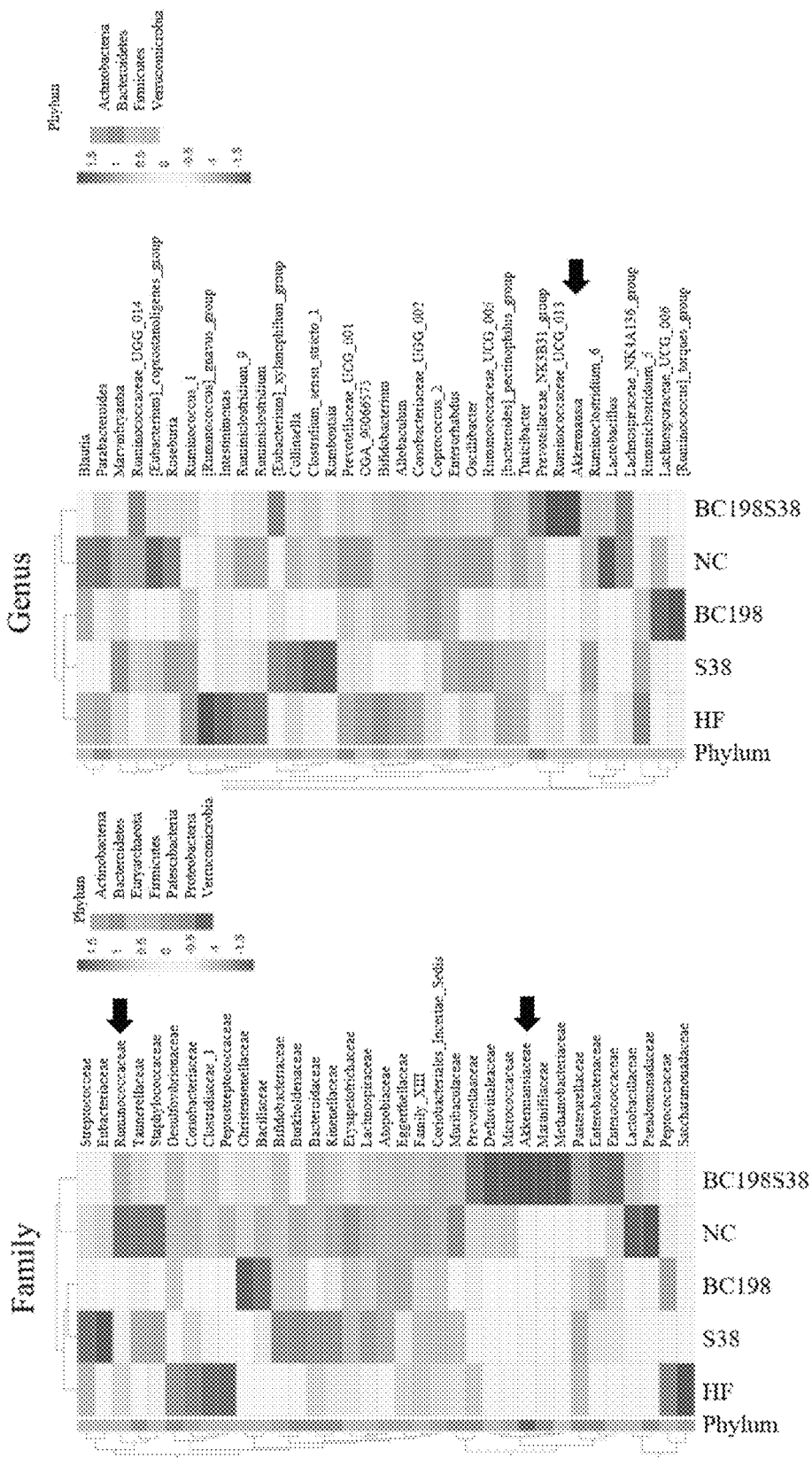
FIG. 8 illustrates the effect of a combination of probiotics on the intestinal microbiota in family and genus levels.

As shown in the content marked by arrows in FIG. 8, the unexpected results are contrary to effects of BC198 or S38 only with administration of both BC198 and S38 conducted.

A combination of probiotics in the present disclosure is characteristic of a low dosage of $5 \times 10^7$ CFU and a high dosage of $5 \times 10^9$ CFU to be administrated to a rat. Referring to the guidance for the human equivalent dose and the body surface area (conversion factor for rat and human=6), the effective doses for administration to a human being with the body weight of 60 kg are $3.2 \times 10^9$ CFU (low dosage) and $3.2 \times 10^{11}$ CFU (high dosage).

A combination of probiotics in the present disclosure comprises a carrier agent, an excipient and a dilutent. A formulation for the combination is selected from a group consisting of a solution, a suspension liquid, an emulsion, a powder, a pastille, a pill, a syrup, a troche, a tablet, a chewing gum, a thick juice and a capsulte. A combination is further manufactured as a liquid milk, a condense milk, a yogurt, a frozen yogurt, a lactobacillus fermented beverage, a milk powder, an ice cream, a cream, a cheese, a soybean milk, a fermented soybean milk, a vegetable juice, a fruit juice, a sports drink, a dessert, a jelly, a candy, a baby food, a healthy food, an animal food, a Chinese herbal medicine composition or a dietary supplement.

The above detailed descriptions are feasible embodiments of a combination of probiotics with *Lacticaseibacillus paracasei* S38 and *Bacillus coagulans* BC198 and applications thereof for improving body composition that should not restrict the scope of the present application and any equivalent implementation or modification without departing from the spirit and scope of the present application should be incorporated in claims hereinafter.

As presented in many effects hereinbefore, a combination of probiotics with *Lacticaseibacillus paracasei* S38 and *Bacillus coagulans* BC198 and applications thereof for improving body composition in the specification meets novelty and non-obviousness for patentability.

Biological Materials Consigned

Information for biological materials deposited with the institution in Taiwan (by institution name, date and number)
1. Food Industry Research and Development Institute; date: Jul. 11, 2019; number: BCRC 910916
2. Food Industry Research and Development Institute; date: Jul. 3, 2020; number: BCRC 911007

Information for biological materials deposited with the institution abroad (by institution name, date and number)
1. German Collection of Microorganisms and Cell Cultures, DSMZ; date: Jul. 103, 2019; number: DSM33206
2. German Collection of Microorganisms and Cell Cultures, DSMZ; date: Jan. 8, 2021; number: DSM33753

Accordingly, it is to be understood that the embodiments of the invention herein described are merely illustrative of the application of the principles of the invention. Reference herein to details of the illustrated embodiments is not intended to limit the scope of the claims, which themselves recite those characteristics regarded as essential to the invention.

What is claimed is:

1. A method for improving body composition in an adult through increase of butyric acid within the intestinal tract of the adult and adjustment of intestinal microbiota in the adult, comprising administering to the adult a combination of probiotics, the combination of probiotics comprising:

*Lacticaseibacillus paracasei* S38 strain deposited under the German Collection of Microorganisms and Cell Cultures (DSMZ) under the number of DSM33753; and

*Bacillus coagulans* BC198 strain deposited under the German Collection of Microorganisms and Cell Cultures (DSMZ) under the number of DSM33206, wherein a dosage of *Lacticaseibacillus paracasei* S38 to be administrated to the adult is $3.2 \times 10^9$ colony forming units (CFU)/day; and a dosage of *Bacillus coagulans* BC198 to be administrated to the adult is $3.2 \times 10^9$ CFU/day, wherein the improving body composition is controlling weight gain and increased body fat or visceral fat after ingestion of a high-fat diet.

2. The method as claimed in claim 1, wherein the improving body composition is effectuated through abatement of appetite and inhibition of lipogenesis.

3. The method as claimed in claim 1, wherein the adjustment of the intestinal microbiota is an increased count or ratio of *Akkermansia muciniphila* or Ruminococcaceae within the intestinal tract after ingestion of a high-fat diet.

* * * * *

SEQUENCE LISTING

<160> NUMBER OF SEQ ID NOS: 2

<210> SEQ ID NO 1
<211> LENGTH: 873
<212> TYPE: DNA
<213> ORGANISM: Lactobacillus sp.

```
<400> SEQUENCE: 1
acgagttctc gttgatgatc ggtgcttgca ccgagattca acatggaacg agtggcggac      60
gggtgagtaa cacgtgggta acctgcccct aagtggggga taacatttgg aaacagatgc     120
taataccgca tagatccaag aaccgcatgg ttcttggctg aaagatggcg taagctatcg     180
cttttggatg gacccgcggc gtattagcta gttggtgagg taatggctca ccaaggcgat     240
gatacgtagc cgaactgaga ggttgatcgg ccacattggg actgagacac ggcccaaact     300
cctacgggag gcagcagtag ggaatcttcc acaatggacg caagtctgat ggagcaacgc     360
cgcgtgagtg aagaaggctt tcgggtcgta aaactctgtt gttggagaag aatggtcggc     420
agagtaactg ttgtcggcgt gacggtatcc aaccagaaag ccacggctaa ctacgtgcca     480
gcagccgcgg taatacgtag gtggcaagcg ttatccggat ttattgggcg taaagcgagc     540
gcaggcggtt ttttaagtct gatgtgaaag ccctcggctt aaccgaggaa gcgcatcgga     600
aactgggaaa cttgagtgca gaagaggaca gtggaactcc atgtgtagcg gtgaaatgcg     660
tagatatatg gaagaacacc agtggcgaag gcggctgtct ggtctgtaac tgacgctgag     720
gctcgaaagc atgggtagcg aacaggatta gataccctgg tagtccatgc cgtaaacgat     780
gaatgctagg tgttggaggg tttccgccct tcagtgccgc agctaacgca ttaagcattc     840
cgcctgggga gtacgaccgc aagttgaact caa                                  873

<210> SEQ ID NO 2
<211> LENGTH: 852
<212> TYPE: DNA
<213> ORGANISM: Bacillus sp.

<400> SEQUENCE: 2
gcagtcgtgc ggaccttta aagcttgctt ttaaaaggtt agcggcggac gggtgagtaa       60
cacgtgggca acctgcctgt aagatcggga taacgccggg aaaccggggc taataccgga    120
tagttttttc ctccgcatgg aggaaaaagg aaagacggct tttgctgtca cttacagatg    180
ggcccgcggc gcattagcta gttggtgggg taacggctca ccaaggcaac gatgcgtagc    240
cgacctgaga gggtgatcgg ccacattggg actgagacac ggcccaaact cctacgggag    300
gcagcagtag ggaatcttcc gcaatggacg aaagtctgac ggagcaacgc cgcgtgagtg    360
aagaaggcct tcgggtcgta aaactctgtt gccggggaag aacaagtgcc gttcgaacag    420
ggcggcgcct tgacggtacc cggccagaaa gccacggcta actacgtgcc agcagccgcg    480
gtaatacgta ggtggcaagc gttgtccgga attattgggc gtaaagcgcg cgcaggcggc    540
ttcttaagtc tgatgtgaaa tcttgcggct caaccgcaag cggtcattgg aaactgggag    600
gcttgagtgc agaagaggag agtggaattc cacgtgtagc ggtgaaatgc gtagagatgt    660
ggaggaacac cagtggcgaa ggcggctctc tggtctgtaa ctgacgctga ggcgcgaaag    720
cgtggggagc aaacaggatt agataccctg gtagtccacg ccgtaaacga tgagtgctaa    780
gtgttagagg gtttccgccc tttagtgctg cagctaacgc attaagcact ccgcctgggg    840
agtacggccg ca                                                         852
```